US006847445B2

United States Patent
Wu

(12) United States Patent
(10) Patent No.: US 6,847,445 B2
(45) Date of Patent: Jan. 25, 2005

(54) METHOD FOR ESTIMATING REPAIR ACCURACY OF A MASK SHOP

(75) Inventor: Yuan-Hsun Wu, Jungli (TW)

(73) Assignee: Nanya Technology Corporation, Taoyuan (TW)

( * ) Notice: Subject to any disclaimer, the term of this patent is extended or adjusted under 35 U.S.C. 154(b) by 392 days.

(21) Appl. No.: 10/035,547

(22) Filed: Nov. 6, 2001

(65) Prior Publication Data

US 2003/0063273 A1 Apr. 3, 2003

(30) Foreign Application Priority Data

Sep. 28, 2001 (TW) ........................................ 90124106 A

(51) Int. Cl.$^7$ ............................. G01N 21/00; G03F 9/00

(52) U.S. Cl. ............................... 356/237.4; 356/237.3; 430/5

(58) Field of Search ........................... 356/237.2–237.5; 430/5

(56) References Cited

U.S. PATENT DOCUMENTS

| 6,023,328 A | * | 2/2000 | Pierrat ..................... 356/237.4 |
| 6,076,465 A | * | 6/2000 | Vacca et al. ................. 101/481 |
| 6,114,073 A | * | 9/2000 | Yang .............................. 430/5 |
| 6,297,879 B1 | * | 10/2001 | Yang et al. .............. 356/237.5 |
| 6,322,935 B1 | * | 11/2001 | Smith ............................ 430/5 |
| 6,335,129 B1 | * | 1/2002 | Asano et al. ................... 430/5 |
| 6,381,356 B1 | * | 4/2002 | Murakami et al. .......... 382/141 |

* cited by examiner

Primary Examiner—Alan Mathews
(74) Attorney, Agent, or Firm—Ladas & Parry LLP

(57) ABSTRACT

The present invention provides a method for estimating repair accuracy of a mask shop. The method comprises the steps of providing a mask having a light-shielding layer with a pattern of a plurality of lines, each of which has a defect, using the mask shop to repair the defects. Contaminated areas are formed in the vicinity of areas where the defects are repaired, measuring first light intensities of the contaminated areas, and second and third light intensities of two sides of the contaminated areas, and calculating ratios of means of the second and third light intensities to the first light intensities to estimate the repair accuracy.

7 Claims, 5 Drawing Sheets

METHOD FOR ESTIMATING REPAIR ACCURACY OF A MASK SHOP

BACKGROUND OF THE INVENTION

1. Field of the Invention

The present invention relates to a method for estimating repair accuracy of a mask shop, which provides a basis for engineers to determine a qualified mask shop.

2. Description of the Prior Art

Masks are frequently used in a semiconductor manufacturing process. A typical mask comprises a transparent substrate such as a quartz substrate and a light-shielding or absorbing layer such as a chrome layer with a thickness of 1000 Å on the substrate. A phase-shift mask further comprises a layer generating a phase shift for the light penetrating therethrough.

A typical mask manufacturing process comprises the steps of depositing a chrome layer on a quartz substrate, depositing a photoresist layer on the chrome layer, patterning the chrome layer by etching under the masking of the photoresist layer processed by e-beam writing and developing.

Defects on the chrome layer are usually generated after the previously described steps. They include clear defects which are missing parts of the chrome layer and opaque defects which are redundant parts of the chrome layer. A further step of chrome depositing is needed to repair the clear defects. As for repair of the opaque defects, a step of chrome sputtering using FIB (Focus Ion Beam) is implemented.

As shown in FIG. 1, the step of chrome depositing is implemented for repairing a clear defect on a line 121 of a chrome layer 12 on a quartz substrate 11. A gentle slope of chrome, rather than a sharp wall, is formed where the clear defect is repaired and some chrome particles are scattered on the quartz substrate 11 in the vicinity of the area where the defect is repaired. Thus, a contaminated area 111 which deteriorates the transparency of the quartz substrate 11 is formed.

The repair accuracy of the mask shop is very important due to the shrinkage of ICs and since defects of the chrome layer always exist. Engineers are eagerly to have a estimation basis of the repair accuracy to determine a qualified mask shop.

SUMMARY OF THE INVENTION

Therefore, the object of the present invention is to provide an estimating method for the repair accuracy for the engineers to determine a qualified mask shop.

The present invention provides a method for estimating repair accuracy of a mask shop. The method comprises the steps of providing a mask having a light-shielding layer with a pattern of a plurality of lines, each of which has a defect, using the mask shop to repair the defects, whereby contaminated areas are formed in the vicinity of areas where the defects are repaired, measuring first light intensities of the contaminated areas, and second and third light intensities of two sides of the contaminated areas, and calculating ratios of means of the second and third light intensities to the first light intensities for estimating the repair accuracy.

Therefore, by using the mask shop to repair the defects on the vertical and horizontal line with different widths, and statistically calculating the errors of the results, the repair accuracy of the mask shop is determined.

BRIEF DESCRIPTION OF THE DRAWINGS

The following detailed description, given by way of example and not intended to limit the invention solely to the embodiments described herein, will best be understood in conjunction with the accompanying drawings, in which.

DETAILED DESCRIPTION OF THE INVENTION

Figure 1:
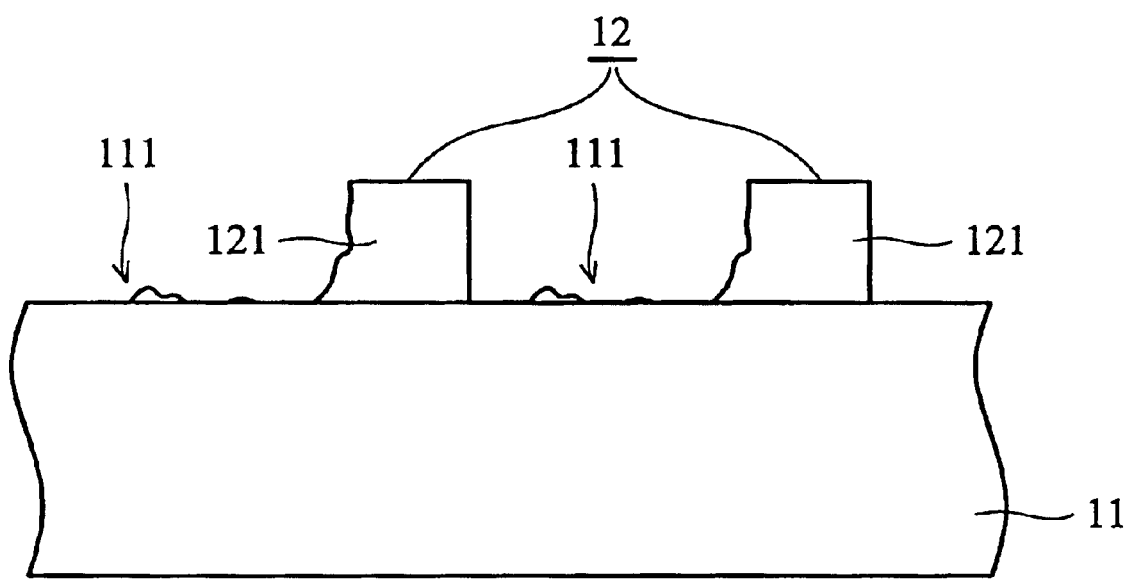
FIG. 1 is a diagram showing a cross section of a mask having a clear defect reoaired.
Figure 2A:
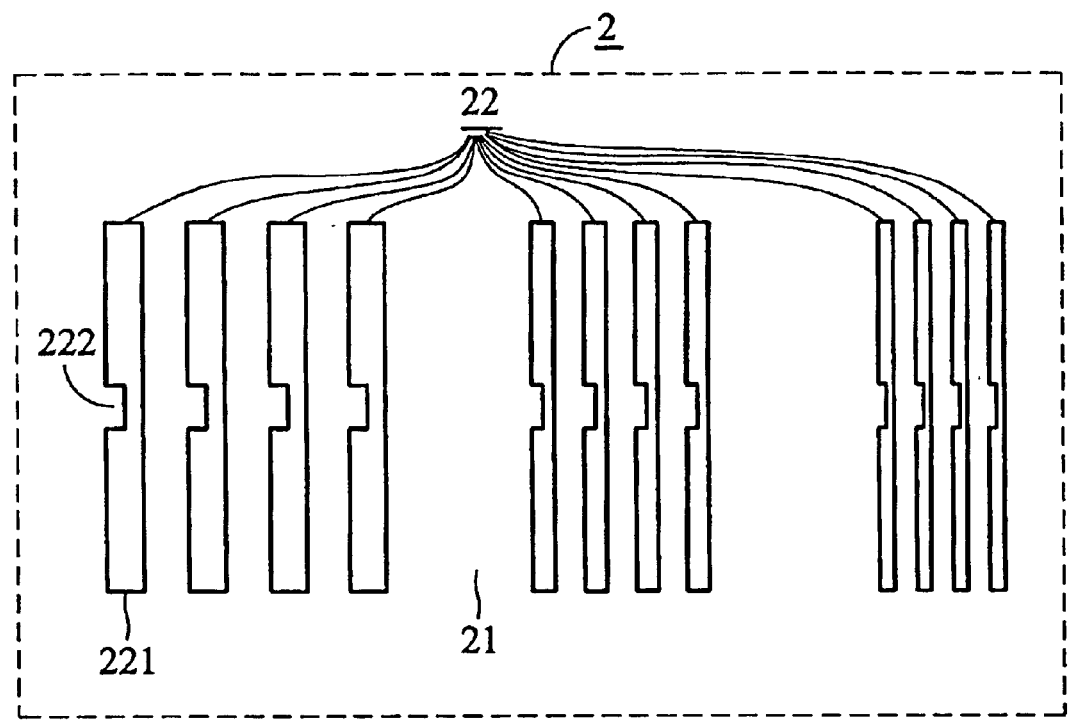
FIGS. 2A and 2B are diagrams showing a pattern of vertical lines on a chrome layer according to one embodiment of the invention.

FIG. 2A is a diagram showing a pattern of vertical lines on a chrome layer of a mask according to a first embodiment of the invention.

The mask comprises a transparent quartz substrate 21 and a chrome layer 22. The chrome layer 22 has a pattern of lines comprising vertical lines 221 with defects 222 which are indentations of the lines 221. The widths of the vertical lines 221 are represented by "a" and the widths of the indented defects 222 along the direction vertical to the lines 221 are 0.5a. The widths a range from 0.5 µm to 2 µm. In this embodiment, the widths a are 0.6, 0.9 and 1.2 µm.

Figure 2B:
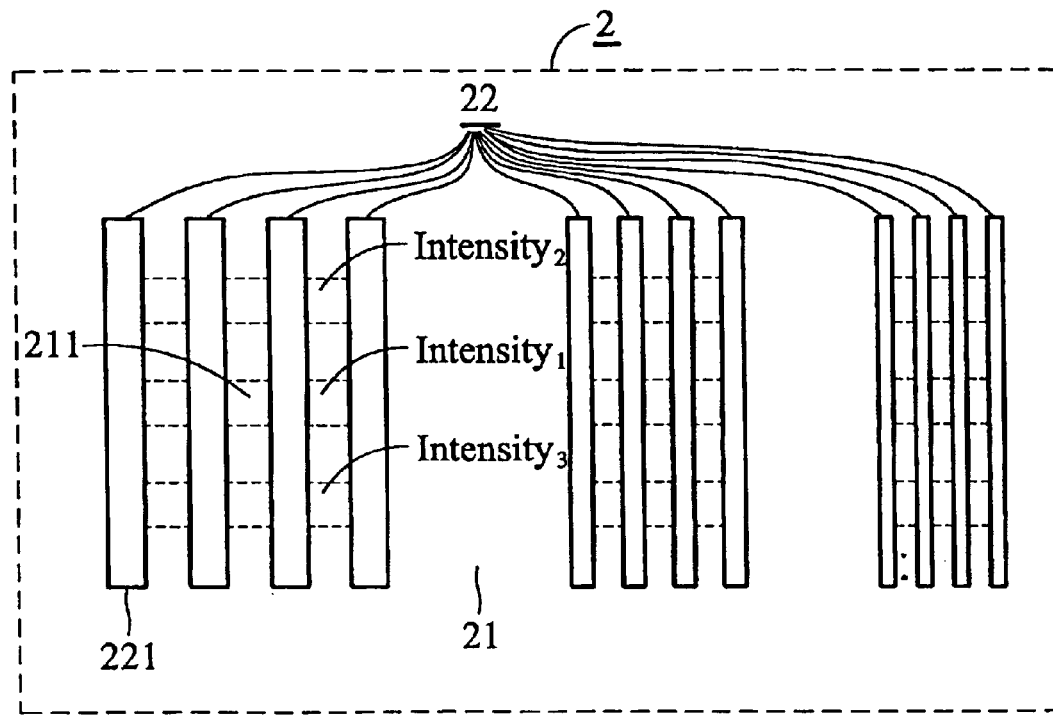

As, shown in FIG. 2B, the defects 222 are filled using a mask shop to be estimated by chrome depositing, whereby contaminated areas 211 are formed on the substrate 21 in the vicinity of areas where the defects 222 are repaired. The light intensities $Intensity_1$ of the contaminated areas 211, and the light intensities $Intensity_2$ and $Intensity_3$ of two sides of the contaminated areas 211 are measured using an Aerial Imaging Measurement System (AIMS), manufactured by Carl Zeiss, with 248-nanometer UV light source and processed with the MSM 100 software. The light intensity values of these areas are compared to nearby reference values to calculate the transmission of the repair in terms of a percent: Ratios $Intensity_{bias}$ for each lines 221 are calculated according to the following equation:

$$Intensity_{bias} = \frac{Intensity_1 - (Intensity_2 + Intensity_3)/2}{(Intensity_2 + Intensity_3)/2}.$$

Therefore, the four ratios $Intensity_{bias}$ are obtained for each group of the lines 221 with width of 0.6, 0.9 and 1.2 µm. A mean and 3 δ value of the ratios $Intensity_{bias}$ are also obtained for each group. Accordingly, the repair accuracy of the mask shop is estimated. The number of the lines 221 is only for example and is usually more than 4 for a statistically effective estimation.

Figure 3A:
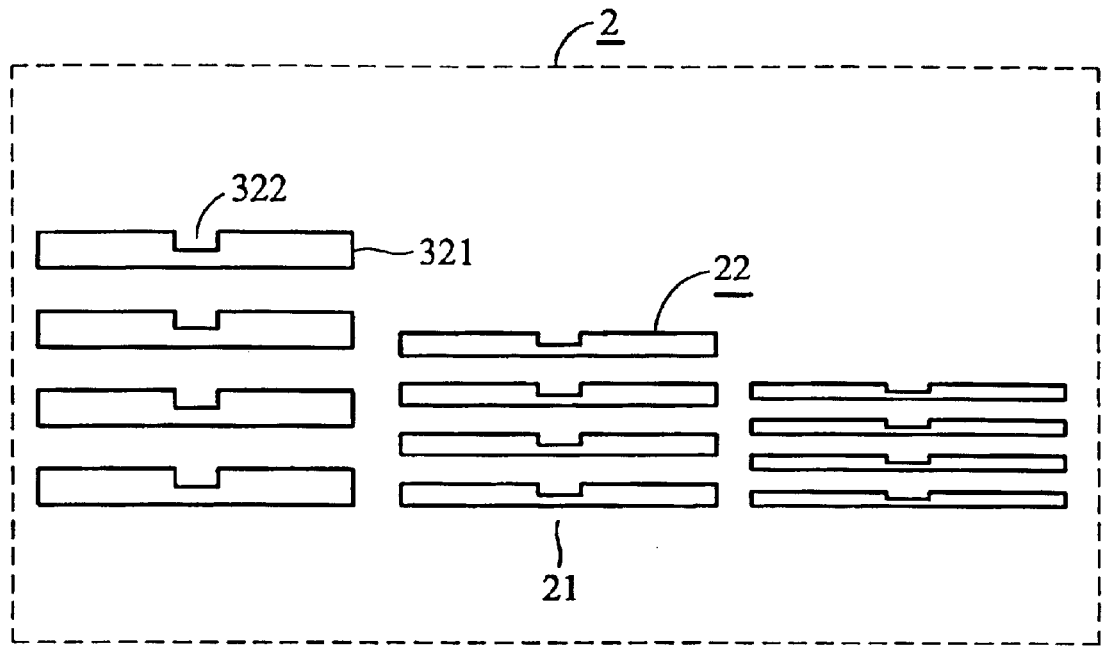
FIGS. 3A and 3B are diagrams showing a pattern of horizontal lines on a chrome layer according to one embodiment of the invention.

FIG. 3A is a diagram showing a pattern of horizontal lines on a chrome layer of a mask according to a second embodiment of the invention. The same elements in FIGS. 2A, 2B, 3A and 3B refer to the same symbol.

The mask comprises a transparent quartz substrate 21 and a chrome layer 22. The chrome layer 22 has a pattern of lines comprising horizontal lines 321 with defects 322 which are indentations of the lines 321. The widths of the horizontal lines 321 are represented by "a" and the widths of the indented defects 322 along the direction vertical to the lines 321 are 0.5a. The widths a range from 0.5 μm to 2 μm. In this embodiment, the widths a are 0.6, 0.9 and 1.2 μm.

Figure 3B:
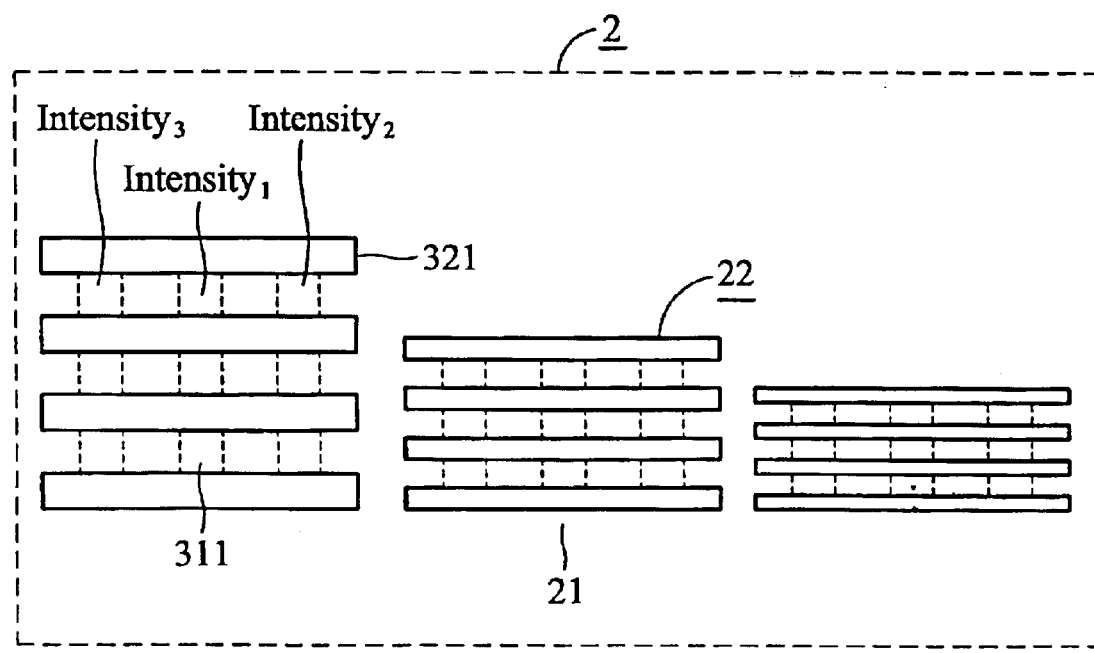

As shown in FIG. 3B, the defects 322 are filled using a mask shop to be estimated by chrome depositing, whereby contaminated areas 311 are formed on the substrate 21 in the vicinity of areas where the defects 322 are repaired. The light intensities $Intensity_1$ of the contaminated areas 311, and the light intensities $Intensity_2$ and $Intensity_3$ of two sides of the contaminated areas 311 are measured. Ratios $Intensity_{bias}$ for each lines 321 are calculated according to the following equation.

$$Intensity_{bias} = \frac{Intensity_1 - (Intensity_2 + Intensity_3)/2}{(Intensity_2 + Intensity_3)/2}.$$

Therefore, the four ratios $Intensity_{bias}$ are obtained for each group of the lines 321 with width of 0.6, 0.9 and 1.2 μm. A mean and 3 sigma value of the ratios $Intensity_{bias}$ are also obtained for each group. The 3 sigma value for each group is the number of ratios located within a range of $\mu \pm 3\sigma$ where σ is the standard deviation of the normal distribution. Accordingly, the repair accuracy of the mask shop is estimated. The number of the lines 321 is only for example and is usually more than 4 for a statistically effective estimation.

Figure 4A:
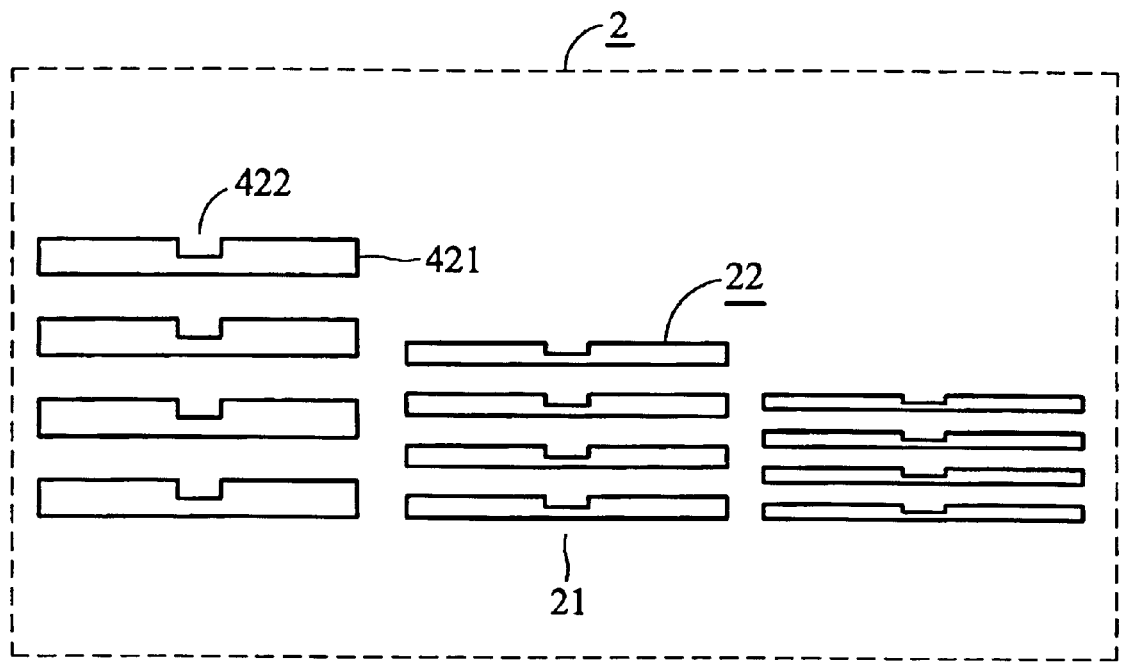
FIGS. 4A and 4B are diagrams showing a pattern of lines having defects with different areas on a chrome layer according to one embodiment of the invention.

FIG. 4A is a diagram showing a pattern of lines with different areas on a chrome layer of a mask according to a third embodiment of the invention. The same elements in FIGS. 2A, 2B, 4A and 4B refer to the same symbol.

The mask comprises a transparent quartz substrate 21 and a chrome layer 22. The chrome layer 22 has a pattern of lines comprising horizontal lines 421 with defects 422 which are indentations of the lines 421. The widths of the horizontal lines 421 are represented by "a" and the widths of the indented defects 422 along the direction vertical to the lines 421 are 0.5a. The widths a range from 0.5 μm to 2 μm. In this embodiment, the widths a are 0.6, 0.9 and 1.2 μm. Additionally, the widths of the indented defects 422 along the direction parallel to the lines 421 are represented by b. The widths b range from 0.3 μm to 1.5 μm. In this embodiment, the widths b are 0.3, 0.5, 0.7 and 1.0 μm.

Figure 4B:
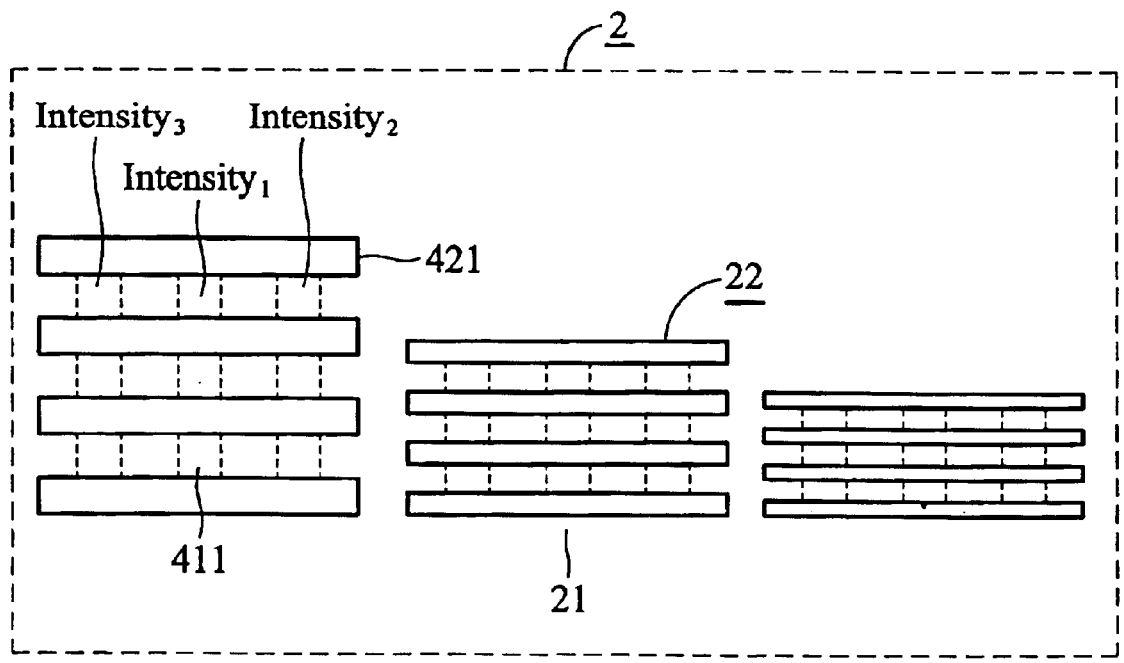

As shown in FIG. 4B, the defects 422 are filled using a mask shop to be estimated by chrome depositing, whereby contaminated areas 411 are formed on the substrate 21 in the vicinity of areas where the defects 422 are repaired. The light intensities $Intensity_1$ of the contaminated areas 411, and the light intensities $Intensity_2$ and $Intensity_3$ of two sides of the contaminated areas 411 are measured. Ratios $Intensity_{bias}$ for each lines 421 are calculated according to the following equation.

$$Intensity_{bias} = \frac{Intensity_1 - (Intensity_2 + Intensity_3)/2}{(Intensity_2 + Intensity_3)/2}.$$

Therefore, the twelve ratios $Intensity_{bias}$ are obtained for each lines 421 respectively with width a of 0.6, 0.9 and 1.2 μm and width b of 0.3, 0.5, 0.7 and 1.0 μm. However, the number of the lines 421 with a certain width a and b is usually more than 1 (here for example) for a statistically effective estimation. In this case, a mean and 3 sigma value of the ratios $Intensity_{bias}$ are also obtained for each group of lines with a certain width a and b. Accordingly, the repair accuracy of the mask shop is estimated.

In the third embodiment, the horizontal lines 421 can be substituted for vertical lines.

Figure 5:
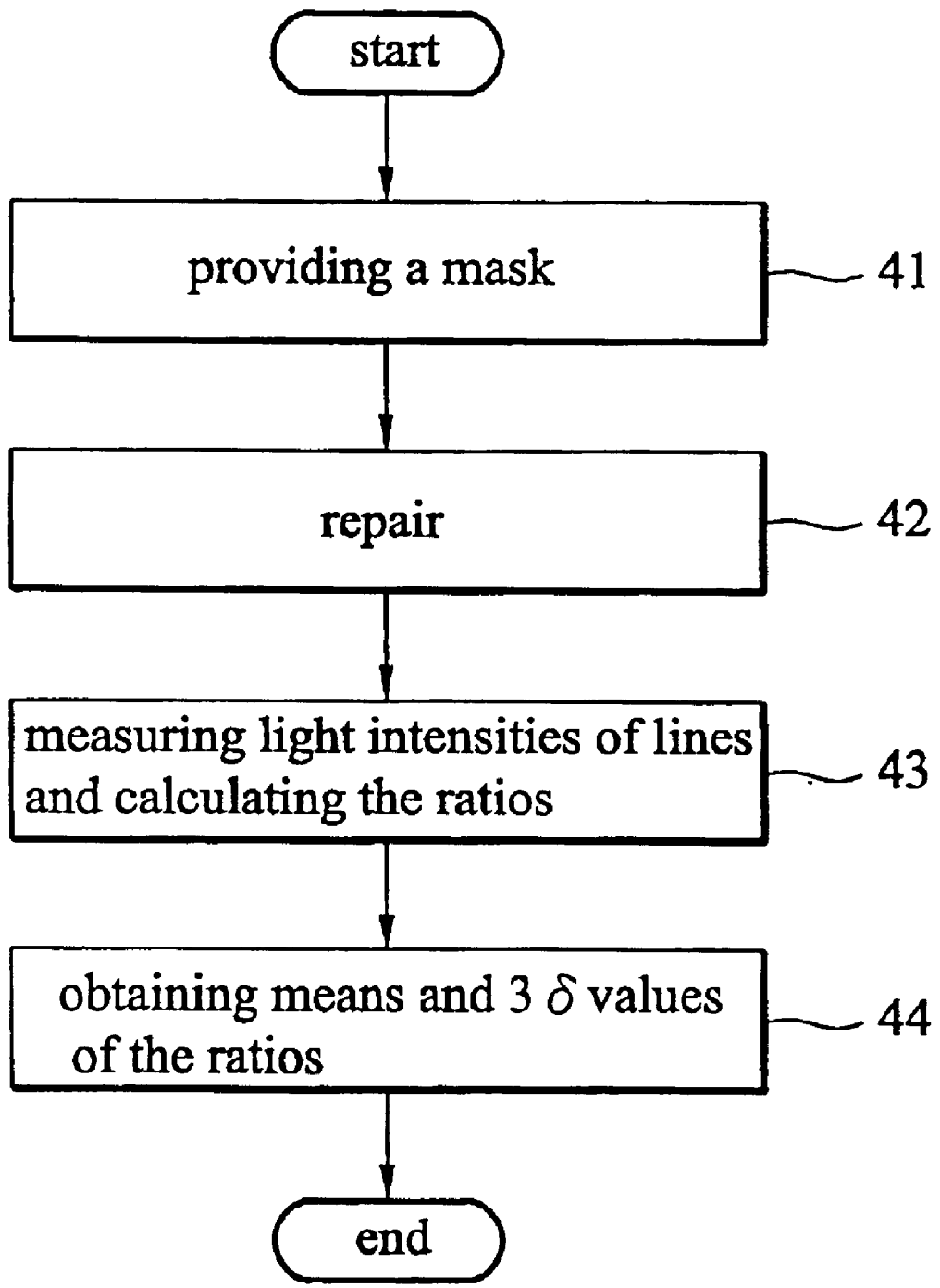
FIG. 5 is a flow chart of a method for estimating repair accuracy of a mask shop according to one embodiment of the invention.

FIG. 5 is a flow chart of a method for estimating repair accuracy of a mask shop according to one embodiment of the invention.

In step 51, a mask comprising a chrome layer having a pattern of vertical and horizontal lines with different widths and indented defects with different areas is provided. The number of the lines with a certain width and defect area is large enough for a statistically effective estimation.

In step 52, the defects are filled using a mask shop to be estimated by chrome depositing, whereby contaminated areas are formed on the substrate in the vicinity of areas where the defects are repaired.

In step 53, the light intensity $Intensity_1$ of the contaminated areas, and the widths $Intensity_2$ and $Intensity_3$ of two sides of the contaminated areas are measured. Ratios $Intensity_{bias}$ for each lines are calculated according to the following equation:

$$Intensity_{bias} = \frac{Intensity_1 - (Intensity_2 + Intensity_3)/2}{(Intensity_2 + Intensity_3)/2}.$$

Finally, in step 54, means and 3 δ values of the ratios $Intensity_{bias}$ for each group of the lines with different widths and defect areas are also obtained. Accordingly, the repair accuracy of the mask shop is estimated.

In conclusion, in the present invention, by using the mask shop to repair the defects on the vertical and horizontal line with different widths and defect areas, and statistically calculating the means and 3 sigma values of the ratios $Intensity_{bias}$ defined in the invention, the repair accuracy of the mask shop is estimated. This provides a basis for engineers to determine a qualified mask shop.

While the invention has been described by way of example and in terms of the preferred embodiment, it is to be understood that the invention is not limited to the disclosed embodiments. On the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method for estimating repair accuracy comprising the steps of:
    providing a mask having a light-shielding layer with a pattern of a plurality of lines, each of which has a defect;
    repairing the defects, whereby contaminated areas are formed in the vicinity of areas where the defects are repaired;
    measuring first light intensities of the contaminated areas, and second and third light intensities of two sides of the contaminated areas; and
    calculating ratios of means of the second and third light intensities to the first light intensities for estimating the repair accuracy.

2. The method as claimed in claim 1 further comprising the step of:
    calculating a mean and 3 sigma value of the ratios.

3. The method as claimed in claim 1 wherein the lines comprise a plurality of vertical and horizontal lines.

4. The method as claimed in claim 3 wherein widths of the lines range from 0.5 μm to 2 μm.

5. The method as claimed in claim 1 wherein widths of the defects along the lines range from 0.3 μm to 1.5 μm.

6. The method as claimed in claim 1 wherein the defects are indentations on the lines.

7. The method as claimed in claim 1 wherein the light-shielding layer is a chrome layer.

* * * * *